United States Patent [19]

Osawa et al.

[11] Patent Number: 5,705,702
[45] Date of Patent: Jan. 6, 1998

[54] METHOD FOR PREPARING TRIARYLSULFONIUM SALTS

[75] Inventors: Yoichi Osawa; Satoshi Watanabe; Junji Shimada; Toshinobu Ishihara, all of Nakakubiki-gun, Japan

[73] Assignee: Shin-Etsu Chemical Co., Ltd., Tokyo, Japan

[21] Appl. No.: 713,257

[22] Filed: Sep. 12, 1996

[51] Int. Cl.⁶ ................................ C07C 331/00
[52] U.S. Cl. .................... 568/77; 568/58; 568/74; 568/75
[58] Field of Search ................ 568/74, 75, 77, 568/58

[56] References Cited

U.S. PATENT DOCUMENTS 4,404,408  9/1983  Wirth et al. ................... 568/77 X

*Primary Examiner*—Paul F. Shaver
*Attorney, Agent, or Firm*—Millen, White, Zelano & Branigan, P.C.

[57] ABSTRACT

By reacting an aryl Grignard reagent of the following general formula (1) with thionyl chloride and then reacting the reaction product with a triorganosilyl sulfonate or triorganohalide of the general formula (2): $(R^6)_3SiY$ wherein $R^6$, which may be the same or different, is a monovalent hydrocarbon group and Y is a substituted or unsubstituted alkylsulfonate or arylsulfonate or halogen atom, there is prepared a triarylsulfonium salt of the following general formula (3).

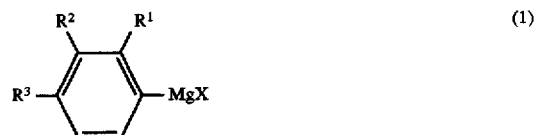

(1)

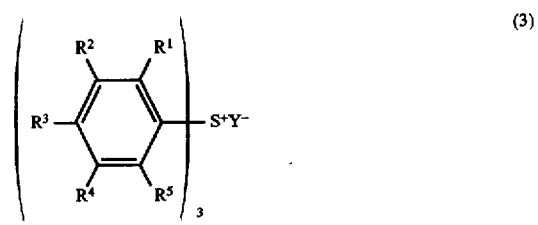

(3)

In the formulae, each of $R^1$ to $R^5$, which may be the same or different, is a hydrogen atom or a monovalent organic group, especially alkyl, aryl, alkoxy, aryloxy, dialkylamino, dialkylaminoalkyl, alkylthio or arylthio group and X is a bromine or chlorine atom.

4 Claims, No Drawings

METHOD FOR PREPARING TRIARYLSULFONIUM SALTS

BACKGROUND OF THE INVENTION

This invention relates to a method for preparing a triarylsulfonium salt which upon absorption of actinic radiation such as deep ultraviolet radiation, excimer laser light, electron beams and X-rays, decomposes to generate an acid to induce condensation reaction or decomposition or elimination reaction and is thus suitable for use in cationic photopolymerization or as a resist material component.

The methods generally used in the prior art for the synthesis of arylsulfonium salts are to condense diaryl sulfoxides with aromatic compounds in the presence of acids (S. Smiles and R. L. Rossignol, J. Chem. Soc., 745 (1908), F. Krollpfeoffer and W. Hahn, Chem. Bet., 86, 1049 (1953), and G. H. Wiegand, W. E. McEwen, J. Org. Chem., 33, 2671 (1968)). These methods are difficult to introduce substituent groups decomposable with acid, that is, acid labile group because condensation reaction is effected under acidic conditions. Where it is desired to introduce a nitrogenous substituent such as dialkylamino groups, an end product is obtained with difficulty because the acid is captured on nitrogen, deprived of electron donative nature and thus deactivated so that nucleophilic attack to the diaryl sulfoxide is unlikely to occur. Also, where a phenol derivative is used as a reagent, there can be formed sulfonium salts having different substitution sites since the phenol has two active sites at the ortho and para-positions.

In addition to the above-mentioned methods, it is also known to react an aryl Grignard reagent with diphenyl sulfoxide after exchanging the solvent for the aryl Grignard reagent such as THF and diethyl ether with an aliphatic/aromatic hydrocarbon solvent such as heptane/benzene (B. S. Wildi, S. W. Taylor and H. A. Potratz, J. Am. Chem. Soc., 73, 1965 (1951)). It was also proposed to react an aryl Grignard reagent with thionyl chloride after exchanging the solvent for the aryl Grignard reagent such as THF and diethyl ether with an aliphatic/aromatic hydrocarbon solvent such as heptane/benzene (Research Disclosure 290,082 (1988)). These methods require complicate steps of first distilling off the THF or diethyl ether solvent for the aryl Grignard reagent and thereafter diluting with heptane/benzene solvent. Additionally, if solvent exchange is insufficient, there arise problems with respect to yield and reproducibility that the percent yield of the arylsulfonium salt is low or the arylsulfonium salt is not synthesized at all.

It was further proposed to react a diaryl sulfoxide with a trialkylsilyl sulfonate at a low temperature and thereafter, reacting with an aryl Grignard reagent (R. D. Miller, A. F. Renaldo and H. Ito, J. Org. Chem., 53,5574 (1988)). This method relies on very complicated temperature control because the respective reagents must be added dropwise at a low temperature of −70° C. and the reaction be ripened at 0° to 10° C. Also needed are a cold bath such as a dry ice/methanol bath and a water bath for reaction ripening. Therefore, low temperature equipment and cumbersome exchange of coolant are necessary and the method is not regarded appropriate from the standpoints of industrial chemistry and cost. Moreover, where a diaryl sulfoxide having an acid labile group is used as a starting reagent in this method, cleavage of the acid labile group occurs owing to acidic impurities in the trialkylsilyl sulfonate, rendering difficult the synthesis of arylsulfonium salts.

Still further, the present inventors previously proposed in U.S. Ser. No. 08/379,987 a method for synthesizing a sulfonium salt having an acid labile group comprising the steps of reacting a diaryl sulfoxide having an acid labile group with a trialkylsilyl sulfonate and reacting the product with an aryl Grignard reagent while adding an organic base such as triethylamine or pyridine to the reaction system for suppressing decomposition of the acid labile group. In this method, however, since the diaryl sulfoxide used as a starting reactant is isolated in low yields, the yield of the sulfonium salt is sometimes low. There also arises a problem that the reaction system can be contaminated with basic impurities since the organic base is used therein. Therefore, it is desired to prepare an end triarylsulfonium salt in high yields without using organic bases. Furthermore, the prior art methods are difficult to carry out all reaction steps in a common reactor because a Grignard reagent is added to the reaction system after it has been prepared in another reactor, and an improvement in this regard is also desired.

SUMMARY OF THE INVENTION

An object of the present invention is to provide a simple method capable of preparing a triarylsulfonium salt in high yields.

The inventors have found that by reacting an excess of an aryl Grignard reagent of the following general formula (1) with thionyl chloride and then reacting the reaction product with a triorganosilyl sulfonate or triorganosilyl halide of the following general formula (2), a triaryl-sulfonium salt of the following general formula (3) can be prepared in high yields without using organic bases. Since all the reaction steps can be carried out in the reactor which has been used to prepare the aryl Grignard reagent, the equipment and process for reaction are simplified.

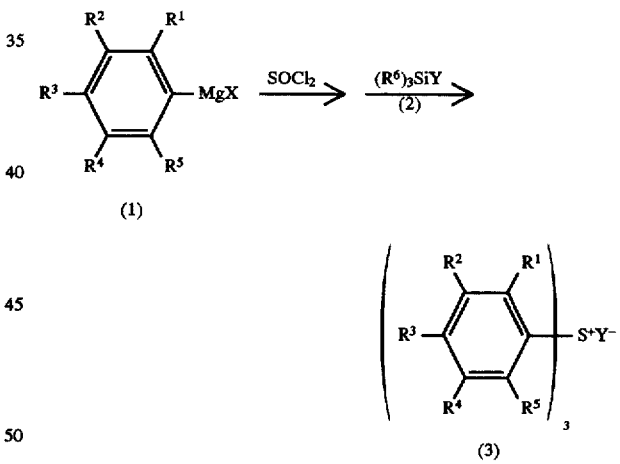

In the formulae, each of $R^1$ to $R^5$, which may be the same or different, is a hydrogen atom or a monovalent organic group; $R^6$, which may be the same or different, is a monovalent hydrocarbon group; X is a bromine or chlorine atom; and Y is a substituted or unsubstituted alkylsulfonate or arylsulfonate or halogen atom.

In preparing a triarylsulfonium salt, the present method uses the aryl Grignard reagent which is a strong base as a stock material, thereby suppressing decomposition of an acid labile group without a need for organic base. Additionally, since the synthesis process eliminates a need for isolation of a sulfoxide compound such as bis(p-tert-butoxyphenyl)sulfoxide and complicated change of cold baths upon dropwise addition of a triorganosilyl sulfonate, all the reaction steps can be carried out in the reactor where the Grignard reagent has been prepared, rendering the process operation very simple.

Therefore, the present invention provides a method for preparing a triarylsulfonium salt, characterized by comprising the steps of reacting an aryl Grignard reagent of the general formula (1) with thionyl chloride and then reacting the reaction product with a triorganosilyl sulfonate or triorganosilyl halide of the general formula (2) for forming a triarylsulfonium salt of the general formula (3).

DETAILED DESCRIPTION OF THE INVENTION

The present invention uses an aryl Grignard reagent which is of the following general formula (1).

(1)

$R^1$ to $R^5$ are a hydrogen atom or monovalent organic group and they may be the same or different. Examples of the monovalent organic group include monovalent hydrocarbon groups having 1 to 14 carbon atoms, especially 1 to 10 carbon atoms (e.g., alkyl and aryl groups); alkoxy groups having 1 to 8 carbon atoms, especially 1 to 6 carbon atoms; acetal or ketal groups having 2 to 8 carbon atoms, especially 2 to 6 carbon atoms; aryloxy groups having 6 to 14 carbon atoms; dialkylamino groups wherein the alkyl moiety has 1 to 6 carbon atoms, especially 1 to 4 carbon atoms; dialkylaminoalkyl groups represented by $R_2N-R'-$ wherein R is an alkyl group having 1 to 6 carbon atoms, especially 1 to 4 carbon atoms and R' is an alkylene group having 1 to 6 carbon atoms, especially 1 to 3 carbon atoms; alkylthio groups having 1 to 8 carbon atoms, especially 1 to 6 carbon atoms; and arylthio groups having 6 to 14 carbon atoms, especially 6 to 10 carbon atoms. X is a bromine or chlorine atom.

It is noted that the alkyl groups represented by $R^1$ to $R^5$ may be normal, branched or cyclic. Examples include methyl, ethyl, propyl, isopropyl, n-butyl, sec-butyl, tert-butyl, hexyl, and cyclohexyl groups. It is preferred to use methyl, ethyl, isopropyl, and tert-butyl groups among them. The alkoxy groups may be normal, branched or cyclic. Examples include methoxy, ethoxy, propoxy, isopropoxy, n-butoxy, sec-butoxy, tert-butoxy, hexyloxy, and cyclohexyloxy groups. It is preferred to use methoxy, ethoxy, isopropoxy, and tert-butoxy groups among others. Examples of the acetal or ketal group include tetrahydropyranyloxy, tetrahydrofuranyloxy, 1-ethoxyethyloxy, and 1-propoxyethoxy groups. It is preferred to use tetrahydropyranyloxy and 1-ethoxyethyloxy groups among others. Examples of the dialkylamino group include N,N-dimethylamino, N,N-diethylamino, N,N-dibutylamino, N,N-dimethylaminoethyl, and N,N-dibutylaminobutyl groups. It is preferred to use a N,N-dimethylamino group among others. Aryl, aryloxy and arylthio groups are also preferably used. Substituents other than the above-mentioned ones may also be used insofar as they can be present stable as Grignard reagents.

The substituted position may be o-, m- or p-position. The m- and p-positions are preferred because it is difficult to obtain an arylsulfonium salt having a substituent with significant steric hindrance at the o-position.

The above-mentioned aryl Grignard reagent can be prepared by a conventional process using an aryl compound of the following formula:

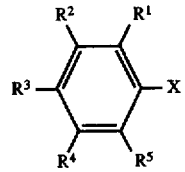

wherein $R^1$ to $R^5$ and X are as defined above and magnesium in an organic solvent such as THF.

The present invention also uses a triorganosilyl sulfonate or triorganosilyl halide which is of the following general formula (2).

$$(R^6)_3SiY \qquad (2)$$

$R^6$ are monovalent, normal, branched or cyclic hydrocarbon groups which may be the same or different. Preferred examples of the monovalent hydrocarbon group include alkyl groups having 1 to 6 carbon atoms, especially 1 to 4 carbon atoms, aryl groups having 6 to 14 carbon atoms, especially 6 to 10 carbon atoms, and aralkyl groups having 7 to 10 carbon atoms, especially 7 to 8 carbon atoms. Alkyl groups are preferred among these.

Y is a substituted or unsubstituted alkylsulfonate or arylsulfonate or halogen atom. For example, it is preferred to use sulfonates such as methanesulfonate, trifluoromethanesulfonate, nonafluorobutanesulfonate, benzenesulfonate, p-toluenesulfonate, 2,4-dimethylbenzenesulfonate, 4-tert-butylbenzenesulfonate, pentafluorobenzenesulfonate, 4-fluorobenzenesulfonate, and 2,2,2-trifluoroethanesulfonate, halogen atoms such as chlorine, bromine, and iodine atoms. For the triorganosilyl sulfonates and triorganosilyl halides using such sulfonates and halogen atoms, mention may be made of, for example, trimethylsilyl chloride, tert-butyldimethylsilyl chloride, triethylsilyl bromide, tert-butyldimethylsilyl bromide, trimethylsilyltrifluoromethane sulfonate, trimethylsilyl-p-toluene sulfonate, trimethylsilyl-4-tert-butylbenzene sulfonate, trimethylsilylnonafluorobutane sulfonate, trimethylsilylbenzene sulfonate, tert-butyldimethylsilyl-p-toluene sulfonate, dimethylisopropylsilyltrifluoromethane sulfonate, trimethylsilyl-2,2,2-trifluoroethane sulfonate, trimethylsilylpentafluorobenzene sulfonate, dimethylphenylsilyltrifluoromethane sulfonate, and triethylsilyl-4-fluorobenzene sulfonate. Preferred among these are trimethylsilyl chloride, tert-butyldimethylsilyl chloride, trimethylsilyltrifluoromethane sulfonate, trimethylsilyl-p-toluene sulfonate, and tert-butyldimethylsilyltrifluoromethane sulfonate.

The triarylsulfonium salt preparing method of the invention favors to add dropwise thionyl chloride alone or in THF to the above-mentioned aryl Grignard reagent in solution form in an organic solvent such as THF solvent used in its preparation or after further dilution with an organic solvent such as THF, to thereby form a diaryl sulfoxide and thereafter, add dropwise the above-mentioned triorganosilyl sulfonate or triorganosilyl halide to the reaction system without isolating the diaryl sulfoxide, that is, to the reaction system where the aryl Grignard reagent remains, thereby synthesizing a triarylsulfonium salt of the following general formula (3):

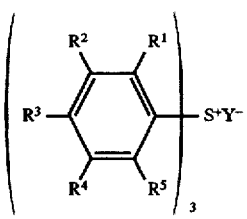

$$\left( \begin{array}{c} R^2 \\ R^3 \\ R^4 \\ R^5 \end{array} \text{---} S^+Y^- \right)_3 \quad (3)$$

wherein $R^1$ to $R^5$ and Y are as defined above.

For reaction of the aryl Grignard reagent with thionyl chloride, it is preferred to use 0.1 to 0.4 mol, especially 0.2 to 0.3 mol of thionyl chloride per mol of the aryl Grignard reagent. Less than 0.1 mol of thionyl chloride would produce a smaller amount of aryl sulfoxide. More than 0.4 mol of thionyl chloride would reduce the amount of the aryl Grignard reagent left after reaction with thionyl chloride, which would eventually reduce the amount of the triarylsulfonium salt produced.

The reaction temperature is preferably −70° C. to 70° C., especially 0° C. to 10° C. At too low reaction temperatures, the aryl Grignard reagent tends to solidify. A large amount of diluent solvent is necessary in order to prevent solidification. If the reaction temperature is too high, a certain type of substituent can be decomposed. Thionyl chloride may be added dropwise as such or after dilution with an organic solvent such as THF. For avoiding a rapid temperature rise by reaction, it is preferred to add dropwise thionyl chloride after dilution. After dropwise addition of thionyl chloride, the reaction is preferably ripened for less than 2 hours, especially ½ to 1 hour.

When the triorganosilyl sulfonate or triorganosilyl halide is added dropwise subsequent to the reaction ripening, it is preferred to add dropwise 0.1 to 1 mol, especially 0.5 to 1 mol of the triorganosilyl sulfonate or triorganosilyl halide per mol of the aryl Grignard reagent. Less than 0.1 mol of the triorganosilyl sulfonate or triorganosilyl halide would produce a smaller amount of the arylsulfonium salt. More than 1 mol of the triorganosilyl sulfonate or triorganosilyl halide has a possibility that when a triarylsulfonium salt having an acid labile group is to be synthesized, decomposition of the acid labile group proceed owing to acidic impurities in the triorganosilyl sulfonate or triorganosilyl halide. The temperature range is desirably −10° C. to 20° C. for the same reason as described with respect to the reaction of thionyl chloride.

The preparation method of the invention permits various functions as a photoacid generator to be introduced into the above-mentioned triarylsulfonium salt by changing the type of substituent on the triarylsulfonium salt.

The triarylsulfonium salt preparing method according to the invention enables to introduce functional substituents into sulfonium salts as in tris(4-tert-butoxyphenyl)-sulfonium salts having a tert-butoxy group which is an acid labile group, tris(3,4-di-tert-butoxyphenyl)sulfonium salts having two tert-butoxy groups which are acid labile groups, and tris(4-dimethylaminophenyl)sulfonium salts having a dialkylamino group as a basic component. Since the sulfonium salt having a tert-butoxy group which is an acid labile group generates an acid upon irradiation of actinic radiation, which acts to decompose the acid labile group to produce a phenol derivative having alkali solubility so that the solubility in aqueous base is different before and after irradiation, this sulfonium salt can be advantageously used as one component of a chemically amplified positive resist composition having a high dissolution contrast and high resolution and suitable for fine patterning technology. The sulfonium salt having an amino group as a basic component is an adequate component of a chemically amplified positive resist composition because it is free of the problems associated with the addition of a simple basic compound including volatilization, poor compatibility, and non-uniform dispersion of the basic compound, and an amino group exerts its effect in a fully reproducible manner. These sulfonium salts are greatly effective, especially in deep-UV lithography.

The triarylsulfonium salt preparing method according to the invention enables the synthesis of triarylsulfonium salts having a functional substituent such as tert-butoxy and dimethylamino groups through a quite simple process in high yields.

EXAMPLE

Examples and Comparative Examples are given below by way of illustration although the invention is not limited to the following Examples.

Example 1

Synthesis of tris(4-tert-butoxyphenyl)sulfonium trifluoromethanesulfonate

A Grignard reagent was conventionally prepared using 60.7 g (2.5 mol) of magnesium, 461 g (2.5 mol) of 4-tert-butoxyphenyl chloride, and 700 g of THF. The Grignard reagent solution was cooled in an ice water bath whereupon 59.5 g (0.5 mol) of thionyl chloride diluted with 100 g of THF was added dropwise at less 30° C. Reaction mixture was ripened for about 30 minutes. Thereafter, 277.8 g (1.25 mol) of trimethylsilyltrifluoromethane sulfonate was added dropwise at less 20° C. Reaction mixture was further ripened for 1 hour and thereafter, the reaction solution was allowed to stand overnight at room temperature. After the reaction solution was again cooled in an ice water bath, 1,800 g of 16.7% ammonium chloride aqueous solution ($NH_4Cl$ 300 g+$H_2O$ 1,500 g) was added thereto at a temperature not in excess of 30° C. After separation, 1,000 g of chloroform was added to the organic layer, which was washed three times using 1,000 g of water. Thereafter, the solvent was distilled off under reduced pressure by means of a rotary evaporator and the resulting oily residue was recrystallized, isolating tris(4-tert-butoxyphenyl)sulfonium trifluoromethanesulfonate of 99% purity in an amount of 141 g (yield 45%).

Comparative Example 1

Synthesis of tris(4-tert-butoxyphenyl)sulfonium trifluoromethanesulfonate

A Grignard reagent which was conventionally prepared using 24.3 g (1 mol) of magnesium, 203.2 g (1.1 mol) of 4-tert-butoxyphenyl chloride, and 280 g of THF was diluted with 500 g of THF and cooled to lower than −60° C. in a dry ice/methanol bath. Then 47.5 g (0.4 mol) of thionyl chloride diluted with 70 g of THF was added dropwise over 1 hour at less 0° C. After ripening for 1 hour in an ice bath, 36 g of water was added to decompose the excess of Grignard reagent. Separation was carried out by adding 1,000 g of methylene chloride and further 400 g of saturated ammonium chloride aqueous solution and 300 g of water. The organic layer was washed twice with 700 g of pure water. The organic layer was dried over magnesium sulfate and filtered and then evaporated. The resulting oily residue was recrystallized, isolating bis(4-tert-butoxyphenyl) sulfoxide in a yield of 60%.

With stirring, 37.8 g (0.17 mol) of (trimethylsilyl)-trifluoromethane sulfonate was added dropwise to a solution of 30.0 g (0.087 mol) of the thus obtained bis(4-tert-butoxyphenyl) sulfoxide and 13.4 g (0.17 mol) of pyridine in 200 g of THF in a controlled manner at less 0° C. With the reaction temperature controlled at 0° to 5° C., the solution was then stirred for 10 minutes.

To the resulting reaction solution, a Grignard reagent which was conventionally prepared using 4.2 g (0.17 mol) of magnesium, 50 g of THF, and 34.3 g (0.19 mol) of 4-tert-butoxyphenyl chloride was added dropwise in a controlled manner at less 0° C.

With the reaction temperature controlled at 0° to 5° C., stirring was continued for a further 60 minutes, completing reaction.

Water was added dropwise to the reaction solution to decompose the excess of Grignard reagent, and the inorganic salt thus formed was removed by filtration. The filtrate was separated using 600 g of methylene chloride, 300 g of saturated ammonium chloride aqueous solution, and 400 g of water. The organic layer was washed twice with 400 g of water and then evaporated, obtaining an oily residue. The oily residue was recrystallized, obtaining tris(4-tert-butoxyphenyl)sulfonium trifluoromethanesulfonate of 99% purity in a yield of 50%. The final yield of this two-steps synthesis process was 30% because the yield was 60% at the first step and 50% at the second step.

Example 2

Synthesis of tris(3,4-di-tert-butoxyphenyl)sulfonium trifluoromethanesulfonate

A Grignard reagent was conventionally prepared using 51.3 g (0.2 mol) of 3,4-di-tert-butoxyphenyl chloride, 4.9 g (0.2 mol) of magnesium, and 100 g of THF. The Grignard reagent solution was cooled in an ice water bath whereupon 5.8 g (0.049 mol) of thionyl chloride diluted with 10 g of THF was added dropwise at less 30° C. Reaction mixture was ripened for about 30 minutes. Thereafter, 26.7 g (0.12 mol) of trimethylsilyltrifluoromethane sulfonate was added dropwise at less 20° C. Reaction mixture was further ripened for 1 hour and thereafter, the reaction solution was allowed to stand overnight at room temperature. After the reaction solution was again cooled in an ice water bath, 200 g of 16.7% ammonium chloride aqueous solution was added thereto at less 30° C. After separation, 100 g of chloroform was added to the organic layer, which was washed three times using 100 g of water. Thereafter, the solvent was distilled off under reduced pressure by means of a rotary evaporator, obtaining an oily residue. The oily residue was recrystallized, isolating tris(3,4-di-tert-butoxyphenyl) sulfonium trifluoromethanesulfonate of 99% purity in an amount of 13.2 g (yield 32%).

Comparative Example 2

Synthesis of tris(3,4-di-tert-butoxyphenyl)sulfonium trifluoromethanesulfonate

A Grignard reagent was conventionally prepared using 3,4-di-tert-butoxyphenyl chloride, magnesium, and THF and further reacted with thionyl chloride, obtaining bis(3,4-di-tert-butoxyphenyl) sulfoxide in a yield of 64%. Then 58.9 g (0.12 mol) of bis(3,4-di-tert-butoxyphenyl) sulfoxide was dissolved in 120 g of THF and cooled in an ice water bath. Then 12.1 g (0.12 mol) of triethylamine was added thereto and 68.3 g (0.31 mol) of trimethylsilyl triflate was added dropwise in a controlled manner at less 10° C. To this solution, a Grignard reagent which was conventionally prepared using 61.6 g (0.24 mol) of 1,2-di-tert-butoxy-4-chlorobenzene, 5.8 g (0.24 mol) of magnesium, and 100 g of THF was added dropwise in a controlled manner at less 10° C. With the reaction temperature controlled at 0° to 10° C., reaction ripening was carried out for 30 minutes. A 20% ammonium chloride aqueous solution, 700 g, was added to the reaction solution to terminate reaction, followed by separation. 300 g of chloroform was added to the organic layer. The organic layer was washed twice using 300 g of water and then evaporated, obtaining an oily residue. The oily residue was worked up by column chromatography (silica gel, eluent: chloroform/methanol), obtaining tris(3,4-di-tert-butoxyphenyl)sulfonium trifluoromethanesulfonate of 99% purity in a yield of 20%. The final percent yield of this two-steps synthesis process was 13%.

Example 3

Synthesis of tris(4-dimethylaminophenyl)sulfonium trifluoromethanesulfonate

A Grignard reagent was conventionally prepared using 100 g (0.5 mol) of 4-bromo-N,N-dimethylaniline, 12.1 g (0.5 mol) of magnesium, and 250 g of THF. The Grignard reagent solution was cooled in an ice water bath whereupon 14.3 g (0.12 mol) of thionyl chloride diluted with 20 g of THF was added dropwise at less 30° C. Reaction mixture was ripened for about 30 minutes. Thereafter, 66.7 g (0.3 mol) of trimethylsilyltrifluoromethane sulfonate was added dropwise at less 20° C. Reaction mixture was further ripened for 1 hour and thereafter, the reaction solution was allowed to stand overnight at room temperature. After the reaction solution was again cooled in an ice water bath, 820 g of 14.6% ammonium chloride aqueous solution was added thereto at less 30° C. After separation, 200 g of chloroform was added to the organic layer, which was washed three times using 200 g of water. Thereafter, the solvent was distilled off under reduced pressure by means of a rotary evaporator and the resulting oily residue was recrystallized, isolating tris(4-dimethylaminophenyl)sulfonium trifluoromethane-sulfonate of 99% purity in an amount of 36.5 g (yield 56%).

Comparative Example 3

Synthesis of tris(4-dimethylaminophenyl)sulfonium trifluoromethanesulfonate

A Grignard reagent was conventionally prepared using 4-dimethylaminophenyl bromide, magnesium, and THF and further reacted with thionyl chloride, obtaining bis(4-dimethylaminophenyl) sulfoxide in a yield of 33%. A solution of 7.0 g (0.024 mol) of the thus obtained bis(4-dimethylaminophenyl) sulfoxide in 100 g of methylene chloride was cooled at −70° C. in a dry ice/methanol bath whereupon with stirring, 6.0 g (0.027 mol) of trimethylsilyl triflate was added dropwise thereto at less −60° C.

The dry ice/methanol bath was then changed to an ice water bath to adjust the reaction temperature at 0° to 5° C., at which stirring was carried out for 10 minutes.

The resulting reaction solution was cooled at −70° C. again using a dry ice/methanol bath. With stirring, a Grignard reagent which was conventionally prepared using 9.9 g (0.049 mol) of 4-bromo-N,N-dimethylaniline, 1.2 g (0.049 mol) of magnesium, and 20 g of THF was added dropwise to the reaction solution at less −60° C.

Next, the bath was changed again to an ice water bath to adjust the reaction temperature at 0° to 5° C., at which stirring was carried out for 60 minutes to complete reaction.

To the reaction solution, 300 g of 15% ammonium chloride aqueous solution was added for separation. The organic layer was washed twice with 150 g of water. The solvent was evaporated under reduced pressure by means of a rotary evaporator, obtaining an oily residue. The oily residue was purified by silica gel column chromatography, obtaining tris(4-dimethylaminophenyl)sulfonium trifluoromethanesulfonate of 99% purity in a yield of 40%. The final yield of this two-steps synthesis process was 13% because the yield was 33% at the first step and 40% at the second step.

Example 4

Synthesis of tris(4-tert-butoxyphenyl)sulfonium p-toluene-sulfonate

A sulfonium salt having p-toluenesulfonic acid as a counter anion was synthesized as in Example 1 except that 305 g (1.25 mol) of trimethylsilyl-p-toluene sulfonate (boiling point 113°–117° C./0.5–0.6 mmHg) which was conventionally obtained using p-toluenesulfonic acid and trimethylsilyl chloride was used instead of 277.8 g of trimethylsilyltrifluoromethane sulfonate in Example 1, obtaining tris(4-tert-butoxyphenyl)sulfonium p-toluenesulfonate of 99% purity in a yield of 45%.

Comparative Example 4

Synthesis of tris(4-tert-butoxyphenyl)sulfonium p-toluene-sulfonate

With stirring, 14.2 g (0.058 mol) of (trimethylsilyl)-p-toluene sulfonate was added dropwise to a solution of 10.0 g (0.029 mol) of bis(4-tert-butoxyphenyl) sulfoxide obtained as in Comparative Example 1 in a yield of 60% and 5.8 g (0.058 mol) of triethylamine in 115 g of THF in a controlled manner at less 0° C. With the reaction temperature controlled at 0° to 5° C., the solution was then stirred for 10 minutes.

To the resulting reaction solution, a Grignard reagent which was conventionally prepared using 1.4 g (0.058 mol) of magnesium, 16 g of THF, and 11.8 g (0.064 mol) of 4-tert-butoxyphenyl chloride was added dropwise in a controlled manner at less 0° C. With the reaction temperature controlled at 0° to 5° C., stirring was continued for a further 60 minutes, completing reaction.

Water was added dropwise to the reaction solution to decompose the excess of Grignard reagent, and the inorganic salt thus formed was removed by filtration. The filtrate was separated using 600 g of methylene chloride, 200 g of saturated ammonium chloride aqueous solution, and 200 g of water. The organic solvent layer was washed three times with 500 g of water and then evaporated, obtaining an oily residue. The oily residue was recrystallized, obtaining tris (4-tert-butoxyphenyl)sulfonium p-toluenesulfonate of 99% purity in a yield of 28%. The final yield was 17% because the yield of the starting sulfoxide as isolated was 60%.

Example 5

Synthesis of tris(4-dimethylaminophenyl)sulfonium p-toluene-sulfonate

A Grignard reagent was conventionally prepared using 100 g (0.5 mol) of 4-bromo-N,N-dimethylaniline, 12.1 g (0.5 mol) of magnesium, and 500 g of THF. The Grignard reagent solution was cooled in an ice water bath whereupon 14.3 g (0.12 mol) of thionyl chloride diluted with 20 g of THF was added dropwise at less 30° C. Reaction was ripened for about 30 minutes. Thereafter, 73.3 g (0.3 mol) of trimethylsilyl-p-toluene sulfonate was added dropwise at less 20° C. Reaction mixture was further ripened for 1 hour and thereafter, the reaction solution was allowed to stand overnight at room temperature. After the reaction solution was again cooled in an ice water bath, 1,500 g of 14.6% ammonium chloride aqueous solution was added thereto at less 30° C. After separation, 400 g of chloroform was added to the organic layer, which was washed three times using 200 g of water. Thereafter, the solvent was distilled off under reduced pressure by means of a rotary evaporator and the resulting oily residue was recrystallized, isolating tris(4-dimethylaminophenyl)sulfonium p-toluenesulfonate of 99% purity in an amount of 39.9 g (yield 59%).

Comparative Example 5

Synthesis of tris(4-dimethylaminophenyl)sulfonium p-toluene-sulfonate

A Grignard reagent was conventionally prepared using 4-dimethylaminophenyl bromide and magnesium in THF solvent and further reacted with thionyl chloride, obtaining bis(4-dimethylaminephenyl) sulfoxide in a yield of 33%.

A solution of 7.0 g (0.024 mol) of the thus obtained bis(4-dimethylaminophenyl) sulfoxide in 200 g of methylene chloride was cooled at −70° C. in a dry ice/methanol bath whereupon with stirring, 6.6 g (0.027 mol) of trimethylsilyl-p-toluene sulfonate was added dropwise thereto at less −60° C.

The dry ice/methanol bath was then changed to an ice water bath to adjust the reaction temperature at 0° to 5° C., at which stirring was carried out for 10 minutes.

The resulting reaction solution was cooled at −70° C. again using a dry ice/methanol bath. With stirring, a Grignard reagent which was conventionally prepared using 10 g (0.05 mol) of 4-bromo-N,N-dimethylaniline, 1.2 g (0.05 mol) of magnesium, and 20 g of THF was added dropwise to the reaction solution at less −60° C.

Next, the bath was changed again to an ice water bath to adjust the reaction temperature at 0° to 5° C., at which stirring was carried out for 60 minutes to complete reaction.

To the reaction solution, 500 g of 15% ammonium chloride aqueous solution was added for separation. The organic layer was washed twice using 200 g of water. The solvent was distilled off from the organic layer under residued pressure by means of a rotary evaporator, obtaining an oily residue. The oily residue was purified by silica gel column chromatography, obtaining tris(4-dimethylaminophenyl) sulfonium p-toluenesulfonate of 99% purity in an amount of 6.1 g (yield 45%).

The yield of this two-steps synthesis process was 15% because the yield was 33% at the first step and 45% at the second step.

Examples 6–9

Synthesis was carried out as in Example 5 except that trimethylsilyl-p-fluorobenzene sulfonate, trimethylsilyl-2,2,2-trifluoroethane sulfonate, trimethylsilylnonafluorobutane sulfonate, and trimethylsilylpentafluorobenzene sulfonate were used instead of trimethylsilyl-p-toluene sulfonate used in Example 5, obtaining end compounds with the yield and purity shown below.

Example 6 tris(4-dimethylaminophenyl)sulfonium p-fluorobenzenesulfonate (purity 99%, yield 55%)

Example 7 tris(4-dimethylaminophenyl)sulfonium 2,2,2-trifluoroethanesulfonate (purity 99%, yield 48%)

Example 8 tris(4-dimethylaminophenyl)sulfonium nonafluorobutanesulfonate (purity 99%, yield 58%)

Example 9 tris(4-dimethylaminophenyl)sulfonium pentafluorobenzenesulfonate (purity 99%, yield 50%)

Comparative Examples 6–9

Synthesis was carried out as in Comparative Example 5 except that trimethylsilyl-p-fluorobenzene sulfonate, trimethylsilyl-2,2,2-trifluoroethane sulfonate, trimethylsilyl-nonafluorobutane sulfonate, and trimethylsilylpentafluorobenzene sulfonate were used instead of trimethylsilyl-p-toluene sulfonate used in Comparative Example 5, obtaining end compounds with the yield and purity shown below.

Comparative Example 6 tris(4-dimethylaminophenyl)sulfonium p-fluorobenzenesulfonate (purity 98%, yield 38%)

The percent yield of this two-steps synthesis process was 13% because the yield was 33% at the first step and 38% at the second step.

Comparative Example 7 tris(4-dimethylaminophenyl)sulfonium 2,2,2-trifluoroethanesulfonate (purity 99%, yield 37%)

The percent yield of this two-steps synthesis process was 12% because the yield was 33% at the first step and 37% at the second step.

Comparative Example 8 tris(4-dimethylaminophenyl)sulfonium nonafluorobutanesulfonate (purity 99%, yield 45%)

The percent yield of this two-steps synthesis process was 15% because the yield was 33% at the first step and 45% at the second step.

Comparative Example 9 tris(4-dimethylaminophenyl)sulfonium pentafluorobenzenesulfonate (purity 99%, yield 41%)

The percent yield of this two-steps synthesis process was 13% because the yield was 33% at the first step and 28% at the second step.

Examples 10–11

Synthesis was carried out as in Examples 1 and 3 except that trimethylsilyl chloride was used instead of trimethylsilyltrifluoromethane sulfonate used in Examples 1 and 3, obtaining end compounds with the yield and purity shown below.

Example 10 tris(4-tert-butoxyphenyl)sulfonium hydrochloride (purity 99%, yield 49%)

Example 11 tris(4-dimethylaminophenyl)sulfonium hydrochloride (purity 99%, yield 50%)

Comparative Examples 10–11

Synthesis was carried out as in Comparative Examples 1 and 3 except that trimethylsilyl chloride was used instead of trimethylsilyltrifluoromethane sulfonate used in Comparative Examples 1 and 3, obtaining end compounds with the yield and purity shown below.

Comparative Example 10 tris(4-tert-butoxyphenyl)sulfonium chloride (purity 98%, yield 40%)

The percent yield of this two-steps synthesis process was 24% because the yield was 60% at the first step and 40% at the second step.

Comparative Example 11 tris(4-dimethylaminophenyl)sulfonium chloride (purity 99%, yield 42%)

The percent yield of this two-steps synthesis process was 14% because the yield was 33% at the first step and 42% at the second step.

Table 1 shows the percent yields of the preparation methods of the foregoing Examples and Comparative Examples.

TABLE 1

| Compound designation | Yield (Example) | Yield (Comparative Example) |
|---|---|---|
| tris(4-tert-butoxyphenyl)sulfonium trifluoromethanesulfonate | 45% | 30% |
| tris(3,4-di-tert-butoxyphenyl)sulfonium trifluoromethanesulfonate | 32% | 13% |
| tris(4-dimethylaminophenyl)sulfonium trifluoromethanesulfonate | 56% | 13% |
| tris(4-tert-butoxyphenyl)sulfonium p-toluenesulfonate | 45% | 17% |
| tris(4-dimethylaminophenyl)sulfonium p-toluenesulfonate | 59% | 15% |
| tris(4-dimethylaminophenyl)sulfonium p-toluenesulfonate | 55% | 13% |
| tris(4-dimethylaminophenyl)sulfonium 2,2,2-trifluoroethanesulfonate | 48% | 12% |
| tris(4-dimethylaminophenyl)sulfonium nonafluorobutanesulfonate | 58% | 15% |
| tris(4-dimethylaminophenyl)sulfonium pentafluorobenzenesulfonate | 50% | 13% |
| tris(4-tert-butoxyphenyl)sulfonium hydrochloride | 49% | 24% |
| tris(4-dimethylaminophenyl)sulfonium hydrochloride | 50% | 14% |

We claim:

1. A method for preparing a triarylsulfonium salt of the following general formula (3):

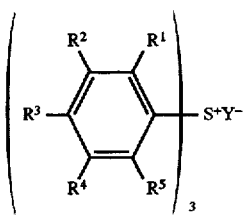

wherein R¹ to R⁵ and Y are as defined below, characterized by comprising the steps of reacting an aryl Grignard reagent of the following general formula (1):

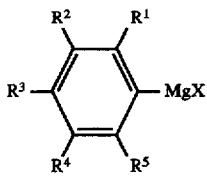

wherein each of $R^1$ to $R^5$, which may be the same or different, is a hydrogen atom or a monovalent organic group and X is a bromine or chlorine atom with thionyl chloride, and then reacting the reaction product with a triorganosilyl sulfonate or triorganosilylhalide of the following general formula (2):

 (2)

wherein $R^6$, which may be the same or different, is a monovalent hydrocarbon group and Y is a substituted or unsubstituted alkylsulfonate or arylsulfonate or halogen atom.

2. A method for preparing a triarylsulfonium salt according to claim 1 wherein each of $R^1$ to $R^5$ in the general formula (1) is a hydrogen atom, alkyl, aryl, alkoxy, acetal, ketal, aryloxy, dialkylamino, dialkylaminoalkyl, alkylthio or arylthio group.

3. A method for preparing a triarylsulfonium salt according to claim 1 wherein 0.1 to 0.4 mol of thionyl chloride is reacted per mol of the aryl Grignard reagent of the general formula (1) and thereafter, 0.1 to 1 mol of the triorganosilyl sulfonate or triorganosilyl halide of the general formula (2) is reacted per mol of the aryl Grignard reagent.

4. A method for preparing a triarylsulfonium salt according to claim 1 wherein thionyl chloride is added to a reactor where the aryl Grignard reagent of the general formula (1) has been prepared and thereafter, the triorganosilyl sulfonate or triorganosilyl halide of the general formula (2) is added to the reactor without isolating the reaction product.

* * * * *